(12) United States Patent
Lemke et al.

(10) Patent No.: US 8,930,220 B2
(45) Date of Patent: Jan. 6, 2015

(54) APPARATUS AND METHODS FOR RENDERING PERSONAL STORIES TO MEDICAL PATIENTS

(75) Inventors: Gilbert Lemke, Los Gatos, CA (US); Debra Lieberman, Santa Barbara, CA (US)

(73) Assignee: Koninklijke Philips N.V., Eindhoven (NL)

( * ) Notice: Subject to any disclaimer, the term of this patent is extended or adjusted under 35 U.S.C. 154(b) by 1005 days.

(21) Appl. No.: 12/596,447

(22) PCT Filed: Apr. 17, 2008

(86) PCT No.: PCT/IB2008/051488
§ 371 (c)(1),
(2), (4) Date: Oct. 19, 2009

(87) PCT Pub. No.: WO2008/129482
PCT Pub. Date: Oct. 30, 2008

(65) Prior Publication Data
US 2010/0131297 A1 May 27, 2010

Related U.S. Application Data

(60) Provisional application No. 60/912,434, filed on Apr. 18, 2007.

(51) Int. Cl.
*G06F 19/00* (2011.01)
(52) U.S. Cl.
CPC .................................... *G06F 19/324* (2013.01)
USPC ............................................................ 705/3
(58) Field of Classification Search
USPC ................ 705/1, 3; 434/238; 707/9; 709/231
See application file for complete search history.

(56) References Cited

U.S. PATENT DOCUMENTS

| 5,879,163 | A | 3/1999 | Brown et al. |
| 5,887,133 | A | 3/1999 | Brown et al. |

(Continued)

FOREIGN PATENT DOCUMENTS

WO 0225551 A1 3/2002

OTHER PUBLICATIONS

Guillen, S., et al.; Multimedia Telehomecare System Using Standard TV Set; 2002; IEEE Trans. on Biomedical Engineering; 49(12)1431-1437.

(Continued)

*Primary Examiner* — John Pauls

(57) ABSTRACT

A health care apparatus (10) and methods are described for rendering audio visual content to a medical patient in the patient's home, in which a content element storage (22) stores a plurality of audio visual content elements (28) to be rendered to the patient in the patient's home, including personal story content elements (40) in which an interviewee (42) is shown discussing one or more issues related to the patient's medical condition. One or more content elements are selected according to a medical condition of a given patient and presented to the patient via a display device (14) of a user interface (12) located in the patient's home. Methods are presented for generating audio visual content for presentation to a medical patient in the patient's home in which a set of questions relating to a given medical condition is generated (102) and questions from the set are presented (104) to at least one interviewee, such as an actor or a person having the given medical condition. The interviewee's responses to the presented questions are recorded (106) and edited (108) to create a personal story content element which is then stored (110) in a content element storage coupled with a communications network from which content elements are selected for presentation to patients having the given medical condition.

24 Claims, 5 Drawing Sheets

(56) References Cited

U.S. PATENT DOCUMENTS

| | | |
|---|---|---|
| 5,897,493 A | 4/1999 | Brown |
| 5,960,403 A | 9/1999 | Brown |
| 5,997,476 A | 12/1999 | Brown |
| 6,101,478 A | 8/2000 | Brown |
| 6,168,563 B1 | 1/2001 | Brown |
| 6,199,114 B1 | 3/2001 | White et al. |
| 6,248,065 B1 | 6/2001 | Brown |
| 6,290,646 B1 | 9/2001 | Cosentino et al. |
| 6,375,469 B1 | 4/2002 | Brown |
| 6,454,705 B1 | 9/2002 | Cosentino et al. |
| 6,723,045 B2 | 4/2004 | Cosentino et al. |
| 6,755,783 B2 | 6/2004 | Cosentino et al. |
| 6,968,375 B1 | 11/2005 | Brown |
| 2002/0133377 A1 | 9/2002 | Brown |
| 2002/0186243 A1 | 12/2002 | Ellis et al. |
| 2002/0188477 A1* | 12/2002 | Ackermann et al. ............... 705/3 |
| 2003/0033157 A1* | 2/2003 | Dempski et al. .................. 705/1 |
| 2003/0069753 A1 | 4/2003 | Brown |
| 2003/0163351 A1 | 8/2003 | Brown et al. |
| 2003/0212579 A1 | 11/2003 | Brown et al. |
| 2004/0019259 A1 | 1/2004 | Brown et al. |
| 2004/0102685 A1 | 5/2004 | Cosentino et al. |
| 2004/0117207 A1 | 6/2004 | Brown |
| 2004/0117208 A1 | 6/2004 | Brown |
| 2004/0117209 A1 | 6/2004 | Brown |
| 2004/0219500 A1 | 11/2004 | Brown et al. |
| 2005/0027562 A1 | 2/2005 | Brown |
| 2005/0080652 A1 | 4/2005 | Brown |
| 2005/0086083 A1 | 4/2005 | Brown |
| 2005/0172021 A1 | 8/2005 | Brown |
| 2005/0172022 A1 | 8/2005 | Brown |
| 2005/0228883 A1 | 10/2005 | Brown |
| 2005/0235060 A1 | 10/2005 | Brown |
| 2005/0273509 A1 | 12/2005 | Brown |
| 2006/0004611 A1 | 1/2006 | Brown |
| 2006/0015017 A1 | 1/2006 | Cosentino et al. |
| 2006/0080152 A1 | 4/2006 | Brown |
| 2006/0089969 A1 | 4/2006 | Brown et al. |
| 2006/0100910 A1 | 5/2006 | Brown |
| 2006/0188859 A1* | 8/2006 | Yakobi ........................ 434/238 |
| 2007/0100829 A1* | 5/2007 | Allen et al. ...................... 707/9 |
| 2008/0005347 A1* | 1/2008 | Ott ................................ 709/231 |

OTHER PUBLICATIONS

"Motiva Fact Sheet" Philips Motiva: Remote Patient Management Platform; Feb. 5, 2007, http://www.medical.philips.com/main/products/telemonitoring/assets/docs/MotivaFactSheet.pdf.

"HU2006 Brochure" p. 16; Feb. 5, 2007, www.tcbi.org/hu2006/folder/TCBI_HU2006_Brochure.pdf.

* cited by examiner

Quiz on Hypoglycemia
When Bill took his blood glucose reading, it was 68 mg/dl.
What should Bill do?
☐ Fast for 15 minutes
☑ Drink a glass of fruit juice
☐ Exercise
☐ Take a nap

FIG. 13

Select Story Teller
Would you like to save this video so that You can view it again another day?
☐ Bill   ☑ Both
☐ Mary

FIG. 14

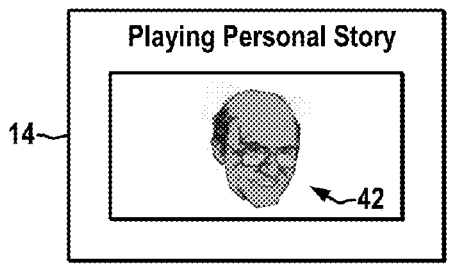

FIG. 15

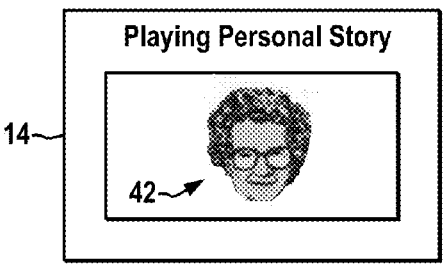

FIG. 16

Congratulations!
You've finished your current goal:
*Understanding Diabetes.*

Press any key for More options

FIG. 17

Home Menu
Messages — Review messages from your Caregiver. You have 6 saved messages.
Logbook
Videos
Points
Settings

FIG. 18

Pick your new goal:
☐ Establish a meal plan
☑ Start an exercise program
☐ Keep a diabetes diary
☐ Skip, go to next activity

FIG. 19

APPARATUS AND METHODS FOR RENDERING PERSONAL STORIES TO MEDICAL PATIENTS

The following relates to ongoing health care for patients with medical conditions such as chronic illnesses, long term medical conditions, etc. In particular, this application involves provision of audio visual content including personal stories to medical patients, preferably in the patient's home or other location remote from a health caregiver via a secure, personalized platform service that connects patients that may not be technologically savvy with their care team to facilitate healthcare organizations effectively and efficiently empowering and assisting patients in managing their health and lifestyle despite the sometimes daunting prospect of dealing with modern technology. The inventors have appreciated that treatment of a patient's medical condition can be aided by modification of the patient's behavior in one or more respects, such as encouraging proper diet and/or exercise, cessation of undesired activities, etc, and further that peer group feedback can facilitate effective behavior modification programs. In this regard, it has been found that patients may respond positively to pertinent information provided by others who are undergoing the same experiences in coping with the same or similar medical problems, and that patients find hope in knowing that they are not alone and that others in the same circumstances have met with success in learning simple techniques and strategies for getting along, and further that peer communication provides patients with moral support.

However, many patients with chronic diseases have limited mobility, and it may be difficult or impossible to get out and participate in live peer group discussions, particularly on a regular basis. While on-line group discussions may be possible, many patients are unfamiliar with the Internet, such as elderly patients who are not well versed in navigating electronic media and thus may forego such opportunities. Memory loss is also often an obstacle to providing care to elderly patients, where certain patients may benefit more from small amounts of information than from participation in lengthy group discussions in which the topic may change frequently. Moreover, certain information obtained in live group settings may be unhelpful or inaccurate, particularly remarks and/or medical advice from non-professionals.

The present disclosure facilitates provision of the positive aspects of peer group feedback to medical patients while mitigating the above negative aspects of attending peer group meetings, particularly for patients with limited ability to travel to live meetings or to participate in on-line sessions.

In accordance with one aspect, a health care apparatus is provided to render audio visual content to a medical patient. The apparatus comprises a content storage coupled with a communications network where the content storage is adapted to store audio visual content elements to be rendered to a medical patient, the content elements including personal story elements that individually include an interviewee shown discussing at least one issue related to a medical condition. The apparatus further includes an itinerary arrangement system operatively coupled with the content storage and adapted to select one or more content elements from the content storage including at least one personal story element to be rendered to the patient in a given viewing session based at least partially on the patient's medical condition. In addition, the apparatus includes a user interface operatively coupled with the network and with a display device, where the user interface is operable by the patient to render the selected content elements to the patient via the display device.

The apparatus advantageously provides the patient with the ability to view content specific video including peer group feedback in the form of personal stories to enhance learning of information related to the patient's medical condition and to facilitate effective behavior modification. The personal story content can be provided along with educational or informative content elements and with interactive survey/quiz content to reinforce the informational content and to aid in information retention. In this manner, the patient can receive relevant information in an interactive television program style setting while remaining in their home and the patient also has the ability to select different presentation options including personal stories told by persons who have encountered similar circumstances in dealing with an illness.

In another aspect, the itinerary arrangement system selects the personal story element and at least one educational content element to be rendered to the patient in a given viewing session and arranges the selected content in a serially ordered itinerary for presentation to the patient with the personal story element presented to the patient after the educational content element. In this arrangement, the personal story can be selected so as to reinforce the educational information provided in a preceding content element, where the personal rendition of the story reiterates some or all of the informative content in the form of a personalized response from a person with whom the patient shares a common connection to enhance the learning experience while providing the motivational and credibility advantages of hearing the information from a person perceived by the patient as a peer. In other possible implementations, survey or quiz type content can be presented along with a personal story in a given viewing session, with the personal story preferably following the survey. In this approach, the personal story can be used to reiterate information related to the survey content. In a related embodiment, the results of an interactive survey or quiz, such as a patient's answer to a survey question, can be used in selecting a personal story presented after the survey. The personal story may thus be used to correct an incorrect answer in the form of a friendly, comforting story to indicate to the patient that others may have misunderstood the same concept, and to relate how others with the same or similar medical conditions have benefited from learning the concept.

In a further aspect, a method is provided for rendering health care information to a patient. The method includes storing audio visual content elements to be rendered to a medical patient in a content element storage coupled with a communications network, including personal story elements individually including an interviewee shown discussing at least one issue related to a medical condition. The method further comprises selecting content elements from the content element storage at least partially according to the patient's medical condition, such as by an itinerary arrangement system coupled with the network, and rendering selected content elements to the patient via a display device of a user interface operatively coupled with the communications network and located in the patient's home.

The content selection and arrangement can include arranging the selected content elements for presentation with the personal story content after one or both of educational and survey content elements, wherein one or more personal story content elements can optionally be selected based at least partially on a patient response to an interactive survey or quiz content element in the viewing session. Certain embodiments of the method, moreover, may include allowing the patient to select from a list of interviewees and selecting a personal story content element showing the selected interviewee discussing at least one issue related to the patient's medical condition. This may facilitate the patient's learning or behavior modification by having the story presented by a person having characteristics preferred by a particular patient, for example, where the interviewees may be characterized by gender, age group, or other group characteristic.

Another aspect is related to a method for generating audio visual content for presentation to a medical patient via a display device of a user interface located in the patient's home and operatively coupled with a communications network. This method includes generating a set of questions relating to a given medical condition, and presenting questions from the set to at least one interviewee, such as by a moderator experienced in encouraging responsiveness in a single interview or group setting. The interviewee responses are recorded and edited, for instance, to remove negative comments, incorrect medical information, responses unrelated to a given medical condition or personal experience, etc., to create a personal story content element and the personal story content is stored in a content element storage coupled with a communications network from which content elements are selected for presentation to patients having the given medical condition. The interviewee can be a person who has or had the given medical condition, or can even be an actor who recreates the substance of responses gleaned from actual patients, such that stories provided by certain patients can be retold to improve grammatical portrayal, to provide the story in a language other than the original interviewee's native language, to provide the story in a dialect or accent more like that of the viewing patient, etc.

This technique allows the end user patient to experience many or all of the advantages of participation in a focus group without having to leave their home, and without having to sit through a lengthy discussion that may involve extraneous or incorrect information.

Another advantage resides in expeditious and economical creation of useful personal story content using responses generated in a group type environment, where the resulting personal story content elements can be categorized and incorporated into the above described content delivery systems for scheduled initial presentation and subsequent recall by the patient.

Still further advantages of the present disclosure will be appreciated to those of ordinary skill in the art upon reading and understand the following detailed description.

The present subject matter may take form in various components and arrangements of components, and in various steps and arrangements of steps. The drawings are only for purposes of illustrating preferred embodiments and are not to be construed as limiting the subject matter, wherein:

FIG. 13 is a schematic diagram illustrating an exemplary survey/quiz question screen rendered to a patient using the apparatus of FIG. 1;

FIG. 14 is a schematic diagram illustrating an exemplary story teller selection screen rendered to a patient using the apparatus of FIG. 1;

FIG. 15 is a schematic diagram illustrating an exemplary personal story viewing screen rendered to a patient using the apparatus of FIG. 1;

FIG. 16 is a schematic diagram illustrating a different personal story viewing screen with a different interviewee telling a story to the patient using the apparatus of FIG. 1;

FIG. 17 is a schematic diagram illustrating an exemplary congratulatory screen rendered to a patient using the apparatus of FIG. 1;

FIG. 18 is a schematic diagram illustrating an exemplary navigational menu screen rendered to a patient using the apparatus of FIG. 1; and FIG. 19 is a schematic diagram illustrating an exemplary user feedback/selection screen rendered to a patient using the apparatus of FIG. 1.

Figure 1:
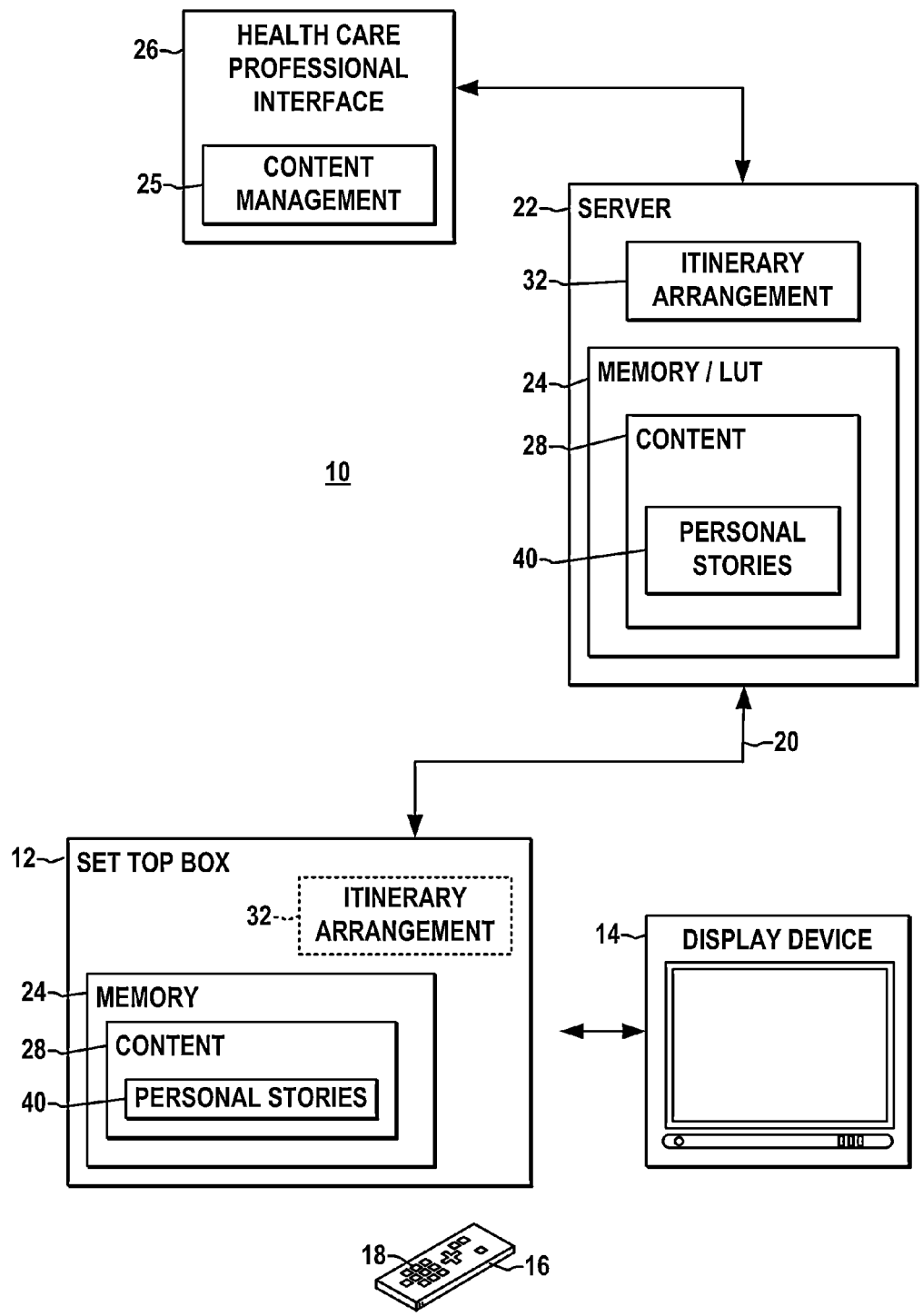
FIG. 1 is a schematic diagram illustrating an exemplary patient healthcare apparatus network in which one or more aspects of the present disclosure may be implemented.

Referring now to the drawings, FIG. 1 schematically depicts an exemplary health care apparatus 10 operable to present or render audio visual personal story content elements to medical patients. Patients with one or more medical conditions often have lifestyle issues which complicate the medical issues, for instance, improper diet, lack of exercise, obesity, smoking, etc. can aggravate diabetes or other medical problem. The apparatus 10 may be advantageously employed to assist patients in managing their disease, adjusting their lifestyle and other behavior modification by providing each patient with personalized programming that can be presented in the patient's home or other convenient setting. In one exemplary implementation, the patient is provided with a care plan in the form of a series of educational or motivational programs directed to healthcare issues specific to that particular patient and their medical condition(s), where the programs include one or more content elements 28. A given patient might be provided, for instance, with educational and motivational programming at the same time each day to assist the patient in establishing and maintaining a diet and exercise regimen. The programming may be provided in any suitable form and format, such as a video disc (e.g., DVD or other format), from a programming memory, or from a central source, such as a content element storage of a networked server 22 operated by a hospital or medical care facility that has prescribed the programming, and the content 28 is transferrable over and/or selectively operable via a public communications network 20 to the patient's home. A set top box or other user operable interface 12 is provided in the patient's home, which decodes the signals intended for the specific patient and displays the corresponding programming on the patient's television or other suitable display device 14 operatively associated with the user interface 12. The patient can interact with the apparatus 10 using their TV or set top box remote controller 16, where the set top box user interface 12 provides for user feedback, such as weigh-ins, blood pressure readings, user selections, etc. to be communicated from the patient to the healthcare facility. In other implementations, the apparatus 10 can be located in a clinic, hospital, school, work site, community center, or other public place.

In certain medical care situations, when a physician prescribes short term care such as a finite amount of prescription drugs, rest, and the like, once the patient takes all the pills, etc., the treatment is in one sense complete. In other possible situations, however, the patient may be diagnosed with a long term illness or chronic disease or other medical condition that requires long term care and/or lifestyle changes. In this scenario, the healthcare professional may prescribe habits or behaviors that were not previously a part of the patient's daily regimen. Motivated by the visit with the doctor, the patient may start the new treatment with good intentions, but may gradually fall back into the prior lifestyle as time goes by. One illustrative example is for diabetes sufferers, where a doctor instructs the patient to eat better, exercise more, and check their insulin levels regularly. Absent further doctor visits or other reminders or motivations, the patient may eventually revert to previous habits by forgetting to diet and exercise, and possibly foregoing regular glucose measurements.

The apparatus 10 may be advantageously employed in such situations to help keep chronic care patients motivated by providing a dynamic care giving experience even long after any given visit to a doctor and to provide health related feedback from the patient to the caregiver. The apparatus 10 is comprised of one or more individual user interface devices 12, one of which is illustrated in FIG. 1, and which can be in the form of a set top box, processor, or other such interface device that is operable by the patient user and which is operatively coupled with the network 20. The user interface 12, moreover, is operatively associated with a display 14, such as the patient's television set, a monitor, or other display device by which audio visual content 28 can be presented or rendered to the patient. In operation of one possible implementation, the patient logs on to the apparatus 10 via the interface device 12, using a handheld remote control device 16, entering information via one or more keys or buttons 18 thereof. The interface 12, moreover, may be a separate set top box connected to the display 14 via suitable cables as shown, or the display 14 may be integrated into the interface 12. The interface device 12 interacts with the input device 16, such as a handheld remote, touch screen, keyboard, mouse, or other similar device by which the patient can enter information, such as passwords, responses to questions, health related readings such as weight or blood pressure, etc. The input device 16 may preferably include large keys 18 with distinct markings such as color, shape, and/or labeling that clearly delineate the intended use or functionality to a patient.

The interface device 12 is operatively coupled with the public network 20, which can be any suitable network, whether wired or wireless or combinations thereof, for example, such as an interactive cable TV network, the internet, etc. Although acting over a public or private network 20, the user interface device 12 communicates with encrypted signals over a secure layer of the network 20 to protect sensitive information of the patient. The interface 12 communicates via the network 20 with various servers such as a server 22 that is remote from the patient location and which preferably is operated by the patient's health care provider, hospital, associated service organization, etc. The exemplary server 22 is operative to store information and/or data and in one example includes a memory such as a look-up-table or database 24 of patient care plans that have been synthesized for all the patients for which this particular server 22 is responsible. A care plan is preferably synthesized by a nurse manager, doctor, or other health care professional based on the patient's medical history. To create a care plan, the health care professional reviews the patient's medical history, and inputs information to a generic care plan template. The system also includes a content management system 25 for uploading, versioning, and previewing content for the health care professional. The content management system 25 also includes a facility to experience what the patient would actually see before actually deploying the media content 28 to the patients.

In one implementation, the health care professional inputs the information to a template via a user interface 26 operatively coupled with the server 22. The templates act as road maps to direct the health care professional in developing the care plan, ensuring that all appropriate questions are addressed. In addition to the template, the health care professional can add features to the care plan based on physician's notes, personality traits of the patient, etc., to further tailor each care plan to an individual patient. The patient's clinician may also have a means such as user interface 26 to see the patient's daily list of media elements to be completed, and may determine when each media item was started, stopped, and status (unopened, in progress, complete, etc.). One, some or all of these factors can be used by the health care professional in initially designing the patient's care plan, or modifying the care plan after the commencement of the care plan.

The server 22 uses the template to compile a care plan for the patient. The server 22 in one embodiment selects specific content elements 28 (videos, surveys, still pictures, audio files, requests for patient input, personal stories 40, etc.) that will be a part of the patient's care plan. The server 22 also decides in what general order the content should be presented to the patient. It is to be understood, however, that ultimately the care plan designer has the option to order the content elements 28 differently, based on type of content, topic, and/or other factors. The care plan designer has the ability to edit media files or the logic branching between files to improve the narrated experience that accompanies the care plan elements on the patient's user interface device 12, including the selective presentation of the personal story content elements 40. The server 22 in one embodiment is in periodic communication with the set top box 12 of a particular patient and receives information and feedback about the patient's progression through the prescribed material on an on-going basis, and may select new content elements for presentation to the patient as they become appropriate. For example, a diabetic patient may initially receive general and overview information about diabetes, and as the patient progresses through that material, the server 22 will select more detailed and specific content directed to the particular patient based both on the care plan template and progress and understanding of the patient. Moreover, the patient may be selectively provided with certain personal story content elements 40 that are scheduled in coordinated fashion with other related content items 28 (e.g., informational and/or survey/quiz content 28), and the selection and/or placement of the personal story content elements 40 in certain implementations can be based at least partially on the patient's responses to survey/quiz questions, input values relating to the patient's condition, etc.

As further illustrated in FIG. 1, the server 22 includes an itinerary arrangement system or component 32, such as hardware, software, or combinations thereof, which operates to select content elements 28 and to arrange the content 28 in an ordered presentation for a given patient viewing session. In other possible implementations, an itinerary arrangement system 32 can be provided as part of the user interface 12, and the interface 12 may also comprise a content element storage memory 24 holding one or more content items 28 including personal stories 40, as well as preassembled care plans, where the health care provider may selectively modify the preloaded plans via the interface 26 and the content management system 25 through communications across the network 20. In such an implementation, the patient may be provided with a set top box 12 preloaded with the content 28 constituting a care plan, with the health care provider being able to access the interface 12 via the network 20 to make schedule changes, arrange content, download further content to the interface 12, etc.

The apparatus 10 of FIG. 1 thus constitutes a health care apparatus operative to render audio visual content to a medical patient. The memory 24 in the server 22 and/or the content storage capacity of the memory 24 in the user interface set top box 12 provide a content element storage coupled with the network 20 for storing a plurality of audio visual content elements 28 including personal story elements 40 to be selectively rendered to a medical patient. An itinerary arrangement system 32 of the server 22 or the user interface 12 is operatively coupled with the content element storage 24 and operates to select one or more content elements 28 from the content element storage 24 including at least one personal story element 40 to be rendered to the patient in a given viewing session based at least partially on the patient's medical condition, where the itinerary arrangement system 32 is preferably adapted to obtain information regarding the patient's medical condition from the content element storage in making the content selection.

The user interface 12 is also coupled with the network 20 and the display device 14, and is operable by the patient to render the selected content elements 28 to the patient via the display device 14. In one exemplary implementation, moreover, the itinerary arrangement system 32 arranges the selected content elements into a serially ordered itinerary for presentation to the patient with the personal story element(s) 40 presented to the patient after an educational content element. Furthermore, the arrangement system 32 may order the content elements such that a personal story content element 40 is presented after an interactive survey/quiz content element, and the personal story content elements 40 can be selected based at least partially on a patient response to an interactive survey or quiz content element 28 in a given viewing session.

As illustrated and described further with respect to FIGS. 14-16 below, moreover, the itinerary arrangement system 32 may be adapted to allow the patient to select from a list of interviewees 42 and to select a personal story content element 40 showing the selected interviewee 42 discussing at least one issue related to the patient's medical condition in order to enhance the patient's experience and the goals of patient learning and/or behavior modification by having the story presented by a person having characteristics preferred by a particular patient, for example, where the interviewees 42 may be characterized by gender, age group, language, or other group characteristic.

Figure 2:
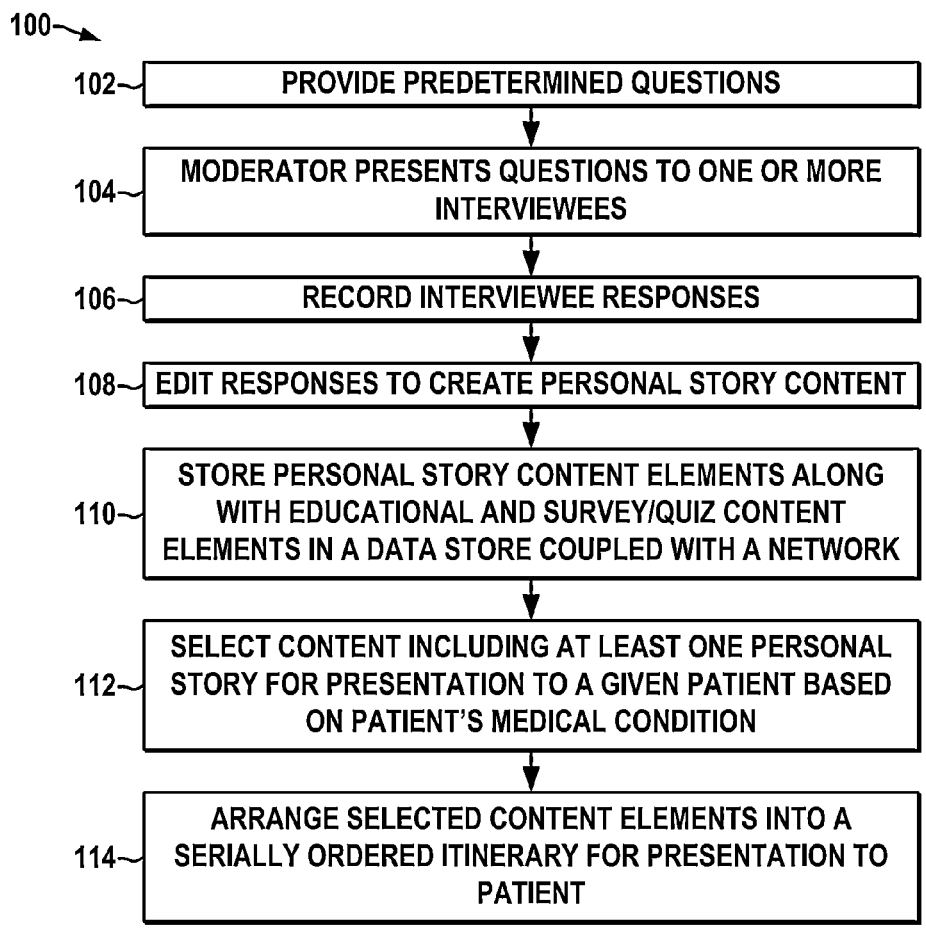
FIG. 2 is a flow diagram illustrating an exemplary method for creating audio visual personal story content elements for presentation to a medical patient in accordance with other aspects of the disclosure.
Figure 3:
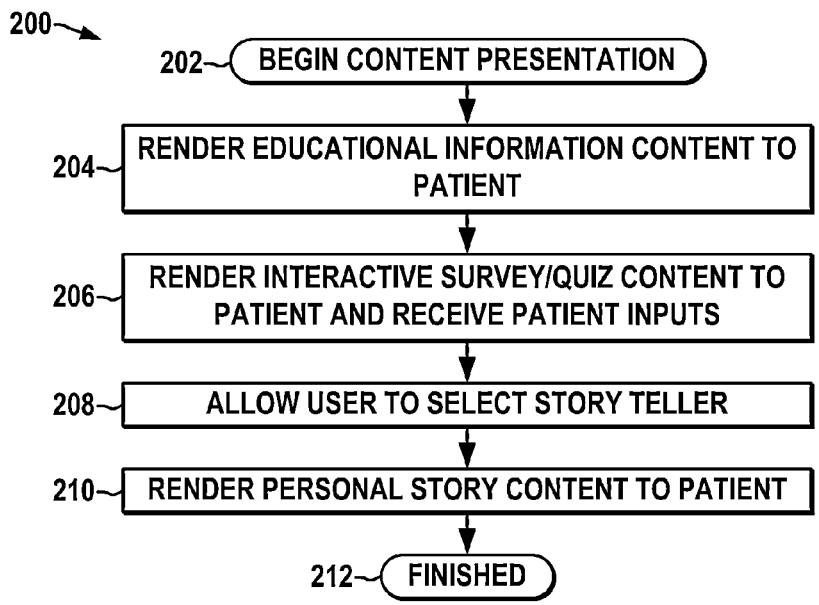
FIG. 3 is a flow diagram illustrating an exemplary method for rendering personal story content to a patient according to the disclosure.
Figure 4:
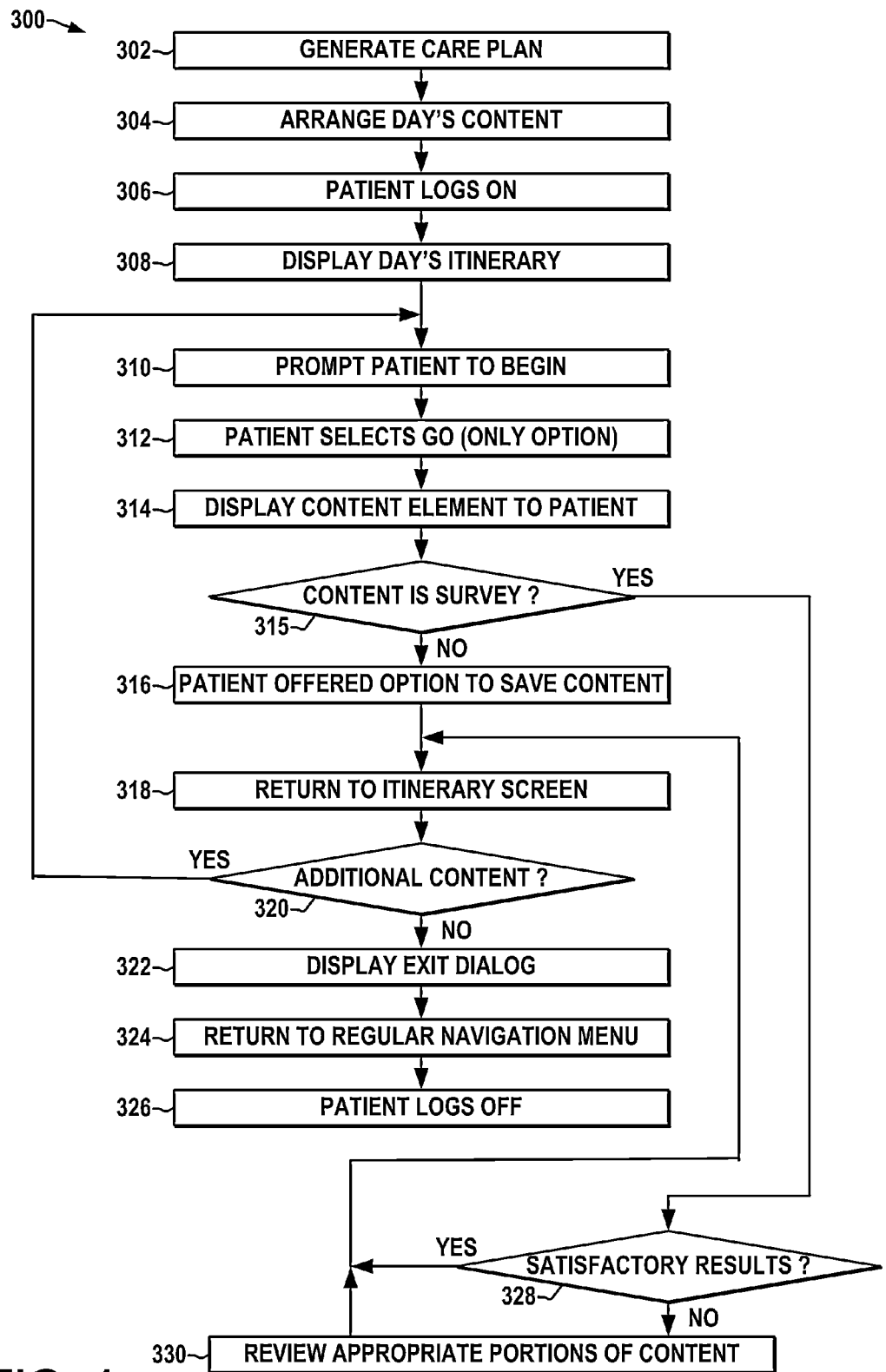
FIG. 4 is a flow diagram illustrating exemplary operation of the apparatus of FIG. 1 in a guided encounter.

Referring also to FIGS. 2-4, the present disclosure provides personal story content elements 40 to a patient to facilitate patient learning, behavior modification, motivation, and the above-described advantages of peer feedback and participation in peer group discussions, while allowing the patient to experience the content in their own home at a time convenient to the patient. Moreover, the apparatus 10 allows the patient to have the personal story content delivered multiple times as desired, whereas participation in live on-line or in-person group discussions offers a one-time-only experience.

FIG. 2 illustrates an exemplary method 100 for creating audio visual personal story content elements for presentation to a medical patient, FIG. 3 depicts an exemplary method 200 for rendering personal story content to a patient, and FIG. 4 illustrates exemplary operation 300 of the apparatus of FIG. 1 in a guided encounter. Although the methods 100, 200, and 300 are illustrated and described in the form of a series of acts or events, it will be appreciated that the various methods of the disclosure are not limited by the illustrated ordering of such acts or events except as specifically set forth herein. In this regard, except as specifically provided hereinafter, some acts or events may occur in different order and/or concurrently with other acts or events apart from those illustrated and described herein, and not all illustrated steps may be required to implement a process or method in accordance with the present disclosure. The illustrated methods may be implemented in hardware, software, manually, or combinations thereof, whether in a network server 22, in the patient user interface device 12, or in other components of the apparatus 10 or the methods may be implemented in distributed form in two or more components or systems, wherein the disclosure is not limited to the specific devices, systems, applications, and implementations illustrated and described herein.

The method 100 of FIG. 2 provides for creation of personal story content elements, wherein a set of predetermined questions is provided at 102 that relate to a given medical condition. In one example, a medical professional might generate a list of topics common to a particular disease or condition at 102, such as diabetes, where an exemplary set of topical questions might relate to a patient taking his or her own blood glucose reading by pricking a finger and using a glucometer, with further questions relating to the patient adjusting their diet in order to keep glucose levels within the proper boundaries, and how exercise affects glucose levels.

At 104, questions from the set are presented to at least one interviewee, and the interviewee responses are recorded at 106. The questions can be obtained in a single-interviewee session or a group of interviewees can be assembled for recordation of a group discussion with a moderator posing questions and interacting with the group. In one example, individual patients are interviewed in their own homes. In another example, a group of diabetes patients could be assembled in a room, along with a moderator, and one or more video camera operators. The moderator in this situation could begin the discussion by asking people to relate their experience of taking their glucose reading for the first time, and following up with questions as to how the patient felt, whether the patient learned any tricks to make the glucose reading easier, how they have incorporated the glucose measurements into their daily lives, etc. In response, one or more interviewees in the group would relate their "personal stories", which are recorded on video. Because of the setting of the interviews and the personal nature of the questions, the responses would be extemporaneous and from the heart, and thus believable and effective for educating and motivating other patients. Prompting by an experienced moderator can advantageously encourage a rich and positive discussion, while focusing the group discussion on a particular topic or medical condition.

While some responses may be very valuable and medically sound, others may not. Accordingly, the interviewee responses are edited at 108 to create a personal story content element including an interviewee 42 shown discussing at least one issue related to a medical condition, as shown below in FIGS. 15 and 16. For instance, the editing at 108 could include removing incorrect or off-topic responses, adjusting the order of responses from a given interviewee, removing extraneous or unintelligible language, removing or filtering portions where more than one person is speaking, etc. The editing also preferably involves removing the interviewee's name or other identifying information in conforming to applicable personal health information requirements or standards to protect interviewees from having their identity disclosed by presentation of a finished personal story content element. The editing, moreover, may include grouping of comment segments according to subject matter and participant.

It is noted that the interviewee can preferably be a person who has or had the given medical condition in order to ensure that the responses are genuine. However, certain responses may not be communicated in a clear manner, or the response may otherwise be unusable while presenting a good story that would benefit subsequent patients. Moreover, the response may include personal health information which will not be included in a finished personal story content element. In such cases, actors can be employed as interviewees, for instance, to recreate an actual interviewee response in whole or in part, or to restate an original interviewee's personal story for creation of usable audio visual personal story content elements 40 while maintaining the interviewee's personal health information confidential. In this respect, it may be desirable to create personal story content using responses in a certain dialect, language, accent, etc., wherein personal story elements can be replicated or recreated using actors capable of producing the desired speech attributes while portraying another (original) interviewee's story and without divulging the real interviewee's identity.

Other possible embodiments of personal story content elements could include a patient or actor speaking directly to the camera so that the content does not appear to be part of an interview response. Alternatively or in combination, an enactment of an event in an interviewee's life could be recorded and in corporate into a personal story content element. For example, the interviewee could speak to an interviewer or to the camera, and the edited video could cut to an enactment of the events being discussed, possibly with the interviewee shown in the enactment.

In other possible embodiments, the interviewee's response could be presented, in whole or in part, as text on the display screen, with or without the interviewee's photo displayed alongside the text. Another possible implementation could include at least portions of the edited interviewee's response being rendered in the form of audio-only personal story elements that could be played while visually rendering an enactment as described above, or text, or other visual content.

At 110 in FIG. 2, the edited content elements are incorporated into the apparatus 10 in FIG. 1, such as by storing the personal story content elements 40 in the content element storage 24 coupled with the communications network 20 from which content elements 28 are selected for presentation to patients having the given medical condition. In the illustrated implementation, the personal story elements 40 are stored along with other types of audio visual content elements 28, such as educational content segments, survey/quiz type interactive content elements, etc., from which a care program can be constructed for a given patient and from which individual viewing sessions can be arranged.

With the content elements 28 stored at 110, one or more content elements 28 are selected at 112 from the content element storage 24 based at least partially on the patient's medical condition, where the selected content elements 28 include at least one personal story element 40 to be rendered to the patient in a given viewing session. In this regard, the method 100 may optionally include obtaining information regarding the patient's medical condition from the content element storage 24 prior to selecting one or more content elements 28 for inclusion in a given viewing session. The content elements 28 can also be selected at 110 based on other considerations, such as general patient background information, the patient's personal information, such as age, gender, progress through a defined care plan, and the like.

At 114, the selected content elements 28 are arranged into a serially ordered itinerary for presentation to the patient. As described above, the ordering of the content elements 28 at 114 may be an initial ordering subject to modification as a viewing session progresses, for example, wherein certain patient responses may trigger the arrangement system 32 to select a specific personal story content element 40 for presentation to the patient. For example, if a patient enters an incorrect answer to a survey or quiz element question, a specific personal story may help to show the patient the correct answer in a friendly way, thus helping to educate the patient while providing the positive reinforcement of having a person explain an issue or the reasoning behind a given survey response in the form of a personal story.

Referring also to FIG. 3, the selected content elements 28 are then rendered or displayed to the patient generally at 200 via the display device 14 associated with the user interface 12 (FIG. 1), beginning at 202. In the example of FIG. 3, educational content elements 28 are rendered initially to the patient at 204, optionally followed by presentation of an interactive survey/quiz type content element 28 at 206. At 208, the user may optionally select from a listing of possible story tellers (e.g., see also FIG. 17 below), after which one or more personal story content elements 40 are rendered to the patient at 210, and the content presentation is finished at 212. In the simplified example of FIG. 3, the rendering of the personal story content 40 at 210 after the educational content at 204 facilitates improved patient retention and learning of the information provided at 204. Moreover, the provision of the personal story 40 at 210 following the survey/quiz content at 206 may advantageously reinforce a correct response to a survey question and/or may provide a friendly way of correcting an incorrect response to facilitate patient understanding. Moreover, the short personal story content elements 40 may be interspersed as is beneficial between informational content and between survey/quiz questions and corresponding patient responses in order to improve the overall learning, information retention, and motivation for a given patient.

In addition to personal stories presented as part of a predefined care program, the apparatus 10 of FIG. 1 may further be adapted to allow a patient to access the personal stories 40 via a central menu rendered on the display device 14. In this implementation, the patient could look over a series of topics, for instance, the use of a glucometer, and could also optionally select a person (story teller) that they would like to hear comments from, as shown for example in FIG. 14 below, allowing selection of someone who the patient feels they can relate to because of similar age, race, gender, etc. For instance, as shown in FIG. 14, a listing may be constructed with names and/or pictures of the possible story tellers for which personal story content elements 40 are available that pertain to a given patient survey response, episode topic, etc. In the illustrated example, the patient is presented with a list showing names for the available story tellers, as well as check boxes allowing patient selection from either "Bill" or "Mary"

or "both". In another possible implementation where multiple story tellers are possible, a list can be constructed to first allow patient selection of story teller age range, gender, region, and/or other characteristics, by which the appropriate personal story content element or elements 40 can be selected for presentation to the patient. Also, the patient may be presented with the option to listen to all of the stories, or all the stories related to a given topic, or all the stories by a given story teller, or other options, and the patient may be allowed to view one or more personal story content elements 40 multiple times if they wish.

Referring now to FIGS. 1 and 4-19, a general description of the overall operation of the exemplary apparatus 10 is presented in the flow chart 300 of FIG. 4, wherein a care plan is initially generated at 302. Before or when the patient logs onto the apparatus 10 via the user interface 12, the display 14, and the remote control 16, the itinerary arrangement system 32 of either the server 22 or the interface device 12 organizes content at 304 for the current day's viewing by the patient into a serially arranged guided encounter. In one implementation using the arrangement system 32 of the network server 22, the server 22 generates the guided encounter at 304 including one or more content elements 28 and transmits the plan to the user interface device 12 in advance of when it is scheduled to be viewed, or as it is to be viewed. Alternatively, the set top box interface 12 can be preloaded and delivered to the patient with a care plan already stored therein. In one embodiment, the server 22 streams content to the user interface device 12 as it is being viewed, or accesses and releases content that is preloaded or stored on the user interface device 12. In another embodiment, an itinerary arrangement processor 32 of the user interface 12 is used, where the server 22 transmits the identity of the preselected content 28 that the patient should view, and the local itinerary arrangement processor 32 in the set top box 12 arranges the content into a guided encounter. When the content 28 is stored locally on the user interface device 12, moreover, the local itinerary arrangement processor 32 takes content that is selected for the present day's viewing, and arranges it into a simple, easy to understand presentation in the form of a guided encounter to be viewed on command by the patient.

Figure 5:
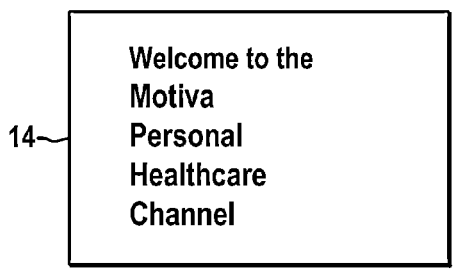
FIG. 5 is a schematic diagram illustrating an exemplary startup screen rendered to a patient using the apparatus of FIG. 1.
Figure 6:
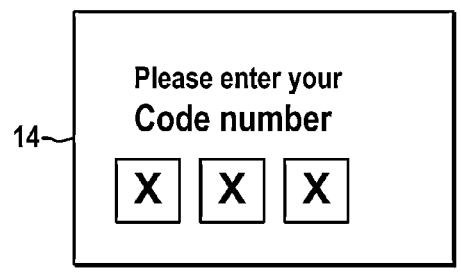
FIG. 6 is a schematic diagram illustrating an exemplary login screen rendered to a patient using the apparatus of FIG. 1.
Figure 7:
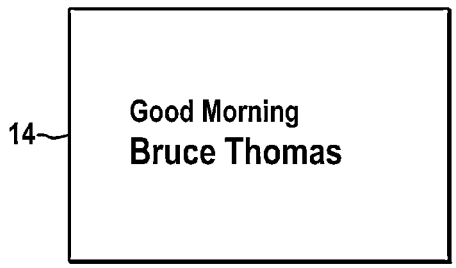
FIG. 7 is a schematic diagram illustrating an exemplary welcome screen rendered to a patient using the apparatus of FIG. 1.
Figure 8:
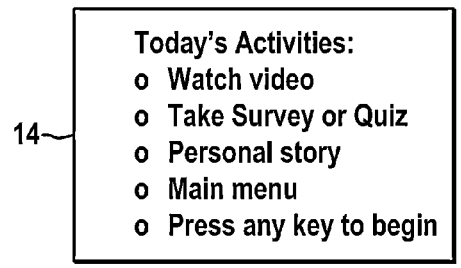
FIG. 8 is a schematic diagram illustrating an exemplary itinerary screen rendered to a patient using the apparatus of FIG. 1.

Once the content elements have been arranged into a guided encounter for the patient, the interface device 12 is prepared to present the guided encounter to the patient. The patient powers up the user interface device 12, and is presented with a welcome screen as shown in FIG. 5, and the patient logs on to the network at 306 by entering a patient identification code into a log on screen (FIG. 6) using the remote control 16, where the code prevents persons other than the patient from accessing the patient's information and programming. The user interface device 12 then presents a welcome screen as shown in FIG. 7 to the patient via the display 14 for several seconds, followed by presentation at 308 of an itinerary screen (FIG. 8), showing the day's scheduled activities. This screen gives the patient an idea of the amount of material that will be covered, where the itinerary may be summarized orally and visually by a nurse narrator and may optionally provide approximate time durations of the material to be presented such that a patient or user can schedule or plan his or her day.

Figure 9:
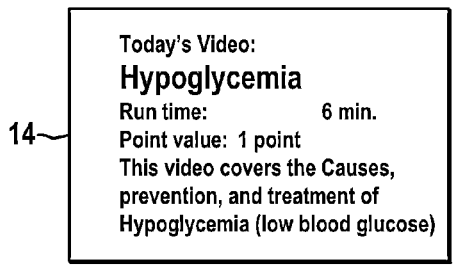
FIG. 9 is a schematic diagram illustrating an exemplary content overview screen rendered to a patient using the apparatus of FIG. 1.
Figure 10:
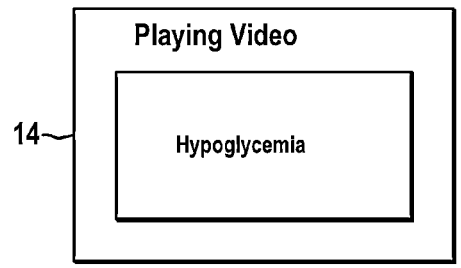
FIG. 10 is a schematic diagram illustrating an exemplary content viewing screen rendered to a patient using the apparatus of FIG. 1.
Figure 11:
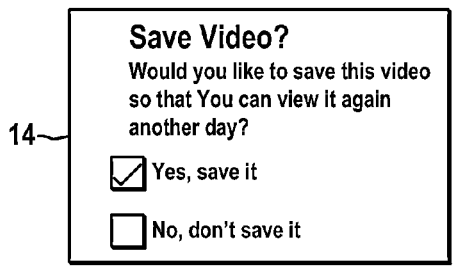
FIG. 11 is a schematic diagram illustrating an exemplary content save option screen rendered to a patient using the apparatus of FIG. 1.
Figure 12:
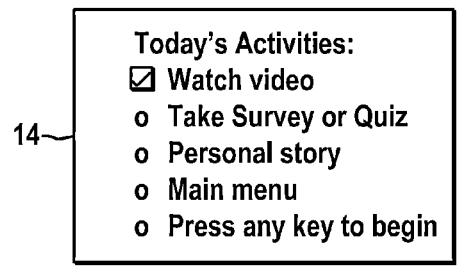
FIG. 12 is a schematic diagram illustrating an exemplary itinerary screen with a partially complete itinerary rendered to a patient using the apparatus of FIG. 1.

At 310, the user interface 12 prompts the patient to begin the presentation, such as by pressing any key 18 on the remote 16 at 312. As shown in FIG. 9, an overview of the first content element is presented, such as showing the title of a video element 28 about hypoglycemia, where the overview screen may include the expected video duration, details about topics covered, etc. The patient then selects to proceed at 312 (FIG. 4), such as by pressing any key 18, and the user interface 12 renders the first content element 28 at 314, such as a hypoglycemia video depicted in FIG. 10. At 315, a determination may be made as to whether the current content element 28 is an interactive survey/quiz type element, and if not (e.g., NO at 315 for an educational content element 28), the patient may be offered the option to save the content element 28 for later review at 316 from a save screen (FIG. 11). Thereafter, the patient is returned to the itinerary screen (FIG. 12) at 318, where the screen may include check marks as shown or other indicia indicating to the patient their relative progress through the material.

The user interface device 12 makes a determination at 320 as to whether there are additional content elements 28 remaining for presentation to the patient in the guided encounter, and if so (YES at 320), returns to 310 and prompts the user to indicate when they are ready to start the next content element 28, such as by pressing any key 18 on the remote controller 16. This process continues at 310-315 as described above, wherein the next element 28 in the illustrated example is a survey or questionnaire or quiz element 28 in which the patient enters one or more responses (YES at 315). As shown in FIG. 13, a survey/quiz screen is presented which requests the patient to answer a question, in this example, after watching the hypoglycemia video. Once the patient provides answers to the survey using the remote 16, the user interface device 12 determines at 328 whether the patient response is correct. If not (NO at 328), appropriate portions of the preceding educational content element 28 may be reviewed at 330, and otherwise, (YES at 328), the user interface returns to the itinerary screen at 318. At 320, the user interface 12 again checks if there is any remaining content.

In the illustrated example, the itinerary screen then indicates that the next content element 28 is a personal story 40, which may have been preselected or may be selected based at least partially on the patient's response to the survey/quiz content 28. In this implementation, moreover, the patient is presented with a story teller selection screen (FIG. 14) at 310, in this case, to select from a first story teller "Bill" or a second story teller "Mary", or to select to hear personal stories 40 from both. The personal story content elements 40 are then rendered to the patient at 314, wherein FIG. 15 illustrates an initial personal story being told to the patient by Bill 42, and FIG. 16 shows another personal story being told by Mary 42.

Once all the scheduled content elements 28 have been presented (NO at 320), the user interface 12 displays an end dialog screen at 322 that congratulates the patient on a successful completion of the guided encounter, an example of which is shown in FIG. 17, after which the patient can press any key 18 to go to a general navigational menu at 324 (FIG. 18) allowing selection of other activities and functions of the system other than those required in the current day's itinerary, and the patient can provide the apparatus 10 with feedback on their own personal goals concerning what they would like to accomplish, as depicted in FIG. 19 or can log off at 326.

The above described examples are merely illustrative of several possible embodiments of the present disclosure, wherein equivalent alterations and/or modifications will occur to others skilled in the art upon reading and understanding this specification and the annexed drawings. In particular regard to the various functions performed by the above described components (assemblies, devices, systems, circuits, and the like), the terms (including a reference to a "means") used to describe such components are intended to correspond, unless otherwise indicated, to any component, such as hardware, software, or combinations thereof, which performs the specified function of the described component (i.e., that is functionally equivalent), even though not structurally equivalent to the disclosed structure which performs the function in the illustrated implementations of the disclosure. In addition, although a particular feature of the disclosure may have been disclosed with respect to only one of several embodiments, such feature may be combined with one or more other features of the other implementations as may be desired and advantageous for any given or particular application. Also, to the extent that the terms "including", "includes", "having", "has", "with", or variants thereof are used in the detailed description and/or in the claims, such terms are intended to be inclusive. It will be appreciated that various of the above-disclosed and other features and functions, or alternatives thereof, may be desirably combined into many other different systems or applications, and further that various presently unforeseen or unanticipated alternatives, modifications, variations or improvements therein may be subsequently made by those skilled in the art which are also intended to be encompassed by the following claims.

Having thus described the preferred embodiments, the invention is now claimed to be:

1. A health care apparatus to render audio visual content to a medical patient, comprising:
    a content element storage coupled with a communications network and adapted to store a plurality of audio visual content elements to be rendered to a medical patient, the plurality of audio visual content elements including a plurality of educational content elements and a plurality of personal story elements, each personal story element including an interviewee shown discussing at least one issue related to a medical condition and wherein the educational content elements include different content from the personal story elements;
    an itinerary arrangement system operatively coupled with the content element storage and adapted to select one or more content elements from the content element storage including at least one of the plurality of educational content elements and at least one of the plurality of personal story elements to be rendered to the patient in a given viewing session based at least partially on the patient's medical condition, wherein the itinerary arrangement system orders the at least one of the plurality of educational content elements for rendering to the medical patient before the at least one of the plurality of personal story elements; and
    a user interface operatively coupled with the communications network and with a display device, the user interface being operable by the patient to render the selected content elements to the patient via the display device.

2. The health care apparatus according to claim 1, wherein the content element storage is located in the user interface.

3. The health care apparatus according to claim 1, wherein the itinerary arrangement system is located in the user interface.

4. The health care apparatus according to claim 1, wherein the itinerary arrangement system selects the at least one of the plurality of personal story elements and at least one of the plurality of educational content elements to be rendered to the patient in a given viewing session based at least partially on the patient's medical condition, and wherein the itinerary arrangement system arranges the selected content elements into a serially ordered itinerary for presentation to the patient with the personal story element presented to the patient after the educational content element.

5. The health care apparatus according to claim 1, wherein the itinerary arrangement system selects the at least one of the plurality of personal story elements and at least one interactive survey or quiz content element to be rendered to the patient in a given viewing session based at least partially on the patient's medical condition, and wherein the itinerary arrangement system arranges the selected content elements into a serially ordered itinerary for presentation to the patient with the personal story element presented to the patient after the interactive survey or quiz content element.

6. The health care apparatus according to claim 5, wherein the itinerary arrangement system selects the at least one personal story element based at least partially on a patient response to the interactive survey or quiz content element in the viewing session.

7. The health care apparatus according to claim 1, wherein the itinerary arrangement system is adapted to obtain information regarding the patient's medical condition from the content element storage to select one or more content elements from the content element storage to be rendered to the patient in a given viewing session.

8. A method of rendering health care information to a patient, comprising:
    storing, by a server, a plurality of audio visual content elements to be rendered to a medical patient, the plurality of audio visual content elements including a plurality of educational content elements and a plurality of personal story elements, each personal story element including an interviewee shown discussing at least one issue related to a medical condition and wherein the educational content elements include different content from the personal story elements;
    selecting, by the server, one or more stored content elements based at least partially on the patient's medical condition, the selected content elements including at least one of the plurality educational content elements and at least one of the plurality of personal story elements to be rendered to the patient in a given viewing session; and
    rendering, by a display device, a display of the selected content elements to the patient, wherein the rendering includes displaying the at least one of the plurality of educational content elements before the at least one of the plurality of personal story elements.

9. The method according to claim 8, wherein the one or more selected stored content elements are transferred to a patient's home for display.

10. The method according to claim 8, wherein selecting one or more content elements includes selecting at least one of the plurality of personal story elements and at least one of the plurality of educational content elements to be rendered to the patient in a given viewing session, and further including arranging the selected content elements into a serially ordered itinerary for presentation to the patient.

11. The method according to claim 8, wherein selecting one or more content elements includes selecting at least one of the plurality of personal story elements and at least one of the plurality of educational content elements or interactive survey or quiz content element to be rendered to the patient in a given viewing session based at least partially on the patient's medical condition, and further including arranging the selected content elements into a serially ordered itinerary for presentation to the patient with the personal story element presented to the patient after the educational content element or the interactive survey or quiz content element.

12. The method according to claim 8, wherein selecting one or more content elements includes selecting at least interactive survey content element and selecting at least personal story element based at least partially on a patient response to the interactive survey content element in the viewing session.

13. The method according to claim 12, wherein selecting one or more content elements includes incorporating at least one personal story content element into a defined care plan.

14. The method according to claim 13, further including arranging the selected content elements into a serially ordered itinerary with the at least one personal story content element arranged to correspond to a chronology of the defined care plan.

15. The method according to claim 8, further comprising obtaining information regarding the patient's medical condition prior to selecting the one or more content elements.

16. The method according to claim 8, further comprising:
generating a set of questions relating to a given medical condition; presenting questions from the set to at least one interviewee; recording the interviewee's responses to the presented questions; editing the interviewee's responses to create a personal story content element; and storing the personal story content element.

17. The method according to claim 16, comprising: gathering a plurality of interviewees in a group session; presenting questions from the set to two or more of the interviewees; recording responses by two or more of the interviewees; and editing the responses to create at least one personal story content element.

18. The method according to claim 8, wherein selecting one or more content elements includes allowing the patient to select from a list of interviewees and selecting a personal story content element showing the selected interviewee discussing at least one issue related to the patient's medical condition.

19. The method according to claim 8, further comprising determining an availability of one or more personal story content elements based on personal information other than the patient's medical condition.

20. A non-transitory computer readable medium or processor programmed to implement a method of rendering health care information to a patient, the method comprising:
storing a plurality of audio visual content elements to be rendered to a medical patient, the plurality of audio visual content elements including a plurality of educational content elements and a plurality of personal story elements, each personal story element including an interviewee shown discussing at least one issue related to a medical condition and wherein the educational content elements include different content from the personal story elements;
selecting one or more stored content elements based at least partially on the patient's medical condition, the selected content elements including at least one of the educational content elements and at least one of the plurality of personal story elements to be rendered to the patient in a given viewing session; and
rendering a display of the selected content elements to the patient, wherein the rendering includes displaying the at least one of the plurality of educational content elements before the at least one of the plurality of personal story elements.

21. A method of rendering health care information to a patient, comprising:
recording, by a recording device, at least one interviewee's responses to at least one question related to a given medical condition;
editing the interviewee's responses to create a personal story content element showing the interviewee discussing the given medical condition;
storing, by a server, an audio visual content element to be rendered to a medical patient, the audio visual content element including an educational content element and the personal story content element, the personal story content element including the interviewee shown discussing at least one issue related to the given medical condition and wherein the educational content element includes different content from the personal story content element;
selecting, by the server, the audio visual content element including the educational content element and the personal story content element to be rendered to the patient in a given viewing session based at least partially on the patient's medical condition; and
rendering, by a display device, a display of the selected audio visual content element to the patient, wherein the rendering includes displaying the educational content element before the personal story element.

22. The method according to claim 21, wherein selecting the audio visual content element includes incorporating the personal story content element into a defined care plan.

23. The method according to claim 22, further including arranging the selected audio visual content element into a serially ordered itinerary with the personal story content element arranged to correspond to a chronology of the defined care plan.

24. The method according to claim 21, further comprising allowing the patient to select from a list of interviewees including the at least one interviewee, and selecting the personal story content element showing the at least one interviewee discussing the at least one issue related to the patient's medical condition.

* * * * *